United States Patent [19]

Shiozaki et al.

[11] Patent Number: 4,562,149

[45] Date of Patent: Dec. 31, 1985

[54] YEAST CULTURE CONTAINING S-ADENOSYL METHIONINE IN HIGH CONCENTRATIONS, AND PROCESS FOR PRODUCTION OF S-ADENOSYL METHIONINE

[75] Inventors: Shozo Shiozaki; Hideaki Yamada; Yoshiki Tani; Sakayu Shimizu, all of Kyoto, Japan

[73] Assignee: Nippon Zeon Co., Ltd., Tokyo, Japan

[21] Appl. No.: 463,990

[22] Filed: Feb. 4, 1983

[30] Foreign Application Priority Data

Feb. 25, 1982 [JP] Japan ................................ 57-29660
Feb. 26, 1982 [JP] Japan ................................ 57-28893

[51] Int. Cl.$^4$ ...................... C12P 13/12; C12P 19/32; C12N 1/16; C12N 1/18
[52] U.S. Cl. ........................................ 435/88; 435/113; 435/255; 435/256; 435/940; 435/942; 435/92
[58] Field of Search ...................... 435/255, 92, 41, 72, 435/84, 85, 87, 106, 113, 243, 256, 813, 942, 940, 88; 426/23

[56] References Cited

U.S. PATENT DOCUMENTS 3,962,034  6/1976  Tsuchida ............................... 435/88

FOREIGN PATENT DOCUMENTS 54-08794  1/1979  Japan .................................... 435/84

OTHER PUBLICATIONS

Kusakabe et al., "Fermentative Production of S-Adenosylmethionine and Glutathione", Chem. Abstr., vol. 79, (1973), p. 308, Abstr. No. 103668j.

Primary Examiner—Thomas G. Wiseman
Assistant Examiner—Jean A. Heck
Attorney, Agent, or Firm—Sherman & Shalloway

[57] ABSTRACT

A yeast culture containing at least 10% by weight, based on the dry cell, of S-adenosyl methionine; and a process for producing S-adenosyl methionine, which comprises cultivating a yeast having the ability to produce S-adenosyl methionine in a liquid culture medium containing methionine to accumulate at least 10% by weight, based on the dry yeast cells, of S-adenosyl methionine in the yeast cells, separating the yeast cells from the culture medium, and thereafter obtaining S-adenosyl methionine in a stable form from the yeast cells.

16 Claims, No Drawings

YEAST CULTURE CONTAINING S-ADENOSYL METHIONINE IN HIGH CONCENTRATIONS, AND PROCESS FOR PRODUCTION OF S-ADENOSYL METHIONINE

This invention relates to microbial cells containing S-adenosyl methionine in a high concentration and adenine related substances and ninhydrin-reactive substances only in low concentrations, and to a process for producing S-adenosyl methionine by which S-adenosyl methionine of high purity can be obtained from such microbial cells with good efficiency by a simple operation.

S-adenosyl methionine (to be abbreviated SAM hereinafter) has been known to be a substance having a therapeutic effect on jecur adipsum, lipemia, arteriosclerosis, etc., and it has recently been desired to produce this substance in large quantities.

One industrial method for producing SAM proposed heretofore comprises cultivating a yeast of the genus Saccharomyces in a liquid culture medium containing methionine, extracting SAM accumulated in the microbial cells, and purifying it [for example, J. Biol. Chem., 229, 1037 (1957)]. In this method, however, the amount of SAM accumulated in the cells is about 3% at the largest, and the extract from the microbial cells is very difficult to purify because it contains large amounts of adenine related substances or ninhydrin-reactive substances which are difficult to separate from SAM. It is especially difficult to separate adenine, S-adenosyl homocysteine and methylthioadenosine. In an attempt to remove this defect, some methods for purifying SAM were proposed (for example, Japanese Patent Publication Nos. 13680/1971, 21079/1974 and 20998/1978, and Japanese Laid-Open Patent Publication No. 145299/1981), but have not proved to be sufficient for obtaining SAM of high purity economically in a high recovery ratio.

A method is also known which comprises cultivating a yeast belonging to the genera Candida, Pichia, Hansenula, Rhodotorula, etc., to form and accumulate SAM in the cells or the culture broth (for example, Japanese Patent Publication No. 17118/1977). In such a method, too, purification of SAM in the microbial cells is difficult, and the recovery of SAM from the culture medium is more difficult since the culture medium contains various metabolites or the decomposition product of SAM in addition to SAM.

Furthermore, since SAM is a very unstable substance, it is often the practice to transport microbial cells containing SAM to a distant place. In this case, the low content of SAM is economically disadvantageous.

In order to remedy the aforesaid defects of the prior art, the present inventors assiduously studied an industrial method for manufacturing SAM by a fermentation technique. This work has finally led to the discovery that when the content of SAM in the microbial cells is increased above a certain level not attainable by the prior art, the amounts of impurities which are present in the microbial cells and are difficult to separate from SAM become very small relative to SAM, and such microbial cells are very easy to purify and SAM of high purity can be economically produced in a high recovery ratio.

In one aspect, the present invention thus provides a microbial cell having accumulated therein at least 10% by weight, based on the weight of the dry cell, of SAM, said cell being obtained by cultivating a microorganism having the ability to produce SAM in a liquid culture medium containing methionine.

In another aspect, the present invention provides a process for producing SAM, which comprises cultivating a microorganism having the ability to produce SAM in a liquid culture medium containing methionine to accumulate at least 10% by weight, based on the weight of the dry cell, of SAM in the microbial cells, separating the microbial cells from the culture medium, and then obtaining SAM in a stable form from the microbial cells.

The microorganism used in this invention may be any microorganism which has the ability to produce SAM and can permit accumulation of at least 10% by weight, based on the dry cells, of SAM in the microbial cells in a liquid medium containing methionine. Yeasts of the genus Saccharomyces are preferred, and yeasts of *Saccharomyces cerevisiae* are especially preferred. Specific examples include *Saccharomyces cerevisiae* IFO 2342, *Saccharomyces cerevisiae* IFO 2343, *Saccharomyces cerevisiae* IFO 2345, *Saccharomyces cerevisiae* IFO 2346, *Saccharomyces cerevisiae* IFO 2347, and Yeast of Sake Kyokai No. 9. Natural and artificial mutants of these strains, which have the above properties, can also be used.

The microbial cell in accordance with this invention contains SAM in an amount of at least 10% by weight, preferably at least 12% by weight, based on the weight of the dry cell.

The microbial cell of this invention is not particularly restricted in respect of a method for its production, and is usually produced by cultivating the microorganism under aerobic conditions in a liquid culture medium containing methionine, carbon sources, nitrogen sources, inorganic salts and very small amounts of organic nutrient sources.

Methionine is added usually in a proportion of at least 0.2 g/dl to the culture medium. Methionine may be added all at a time, or successively in divided portions. If, however, the former procedure is taken when the amount of methionine added is large, the amount of SAM accumulated in the microbial cell tends to decrease. In such a case, it is proper to use the latter procedure.

Examples of the carbon sources are sugars such as glucose, sucrose and fructose, alcohols such as ethanol and glycerol, starch hydrolyzate, molasses, soybean whey, fruit juice waste liquor, fish processing waste liquor, fermentation waste liquor, and pulp spent liquor. Preferred nitrogen sources include urea, ammonium succinate, ammonium citrate, ammonium lactate, trimethylenediamine, tetramethylenediamine, spermine, spermidine, and 3-amino-1,2,4-triazole.

Ordinary inorganic salts may be used as required. Examples include phosphates such as potassium phosphate, sodium phosphate, calcium phosphate and lithium phosphate; potassium salts such as potassium chloride; sodium salts such as sodium chloride and sodium carbonate; magnesium salts such as magnesium sulfate and magnesium chloride; manganese salts such as manganese sulfate and manganese chloride; iron salts such as iron sulfate and iron chloride; zinc salts; copper salts; and cobalt salts.

Examples of organic nutrient sources which may be used as required include vitamins, amino acids, yeast extract, meat extract, malt extract, corn steep liquor, Casamino acid, soybean meal, soybean hydrolyzate, peptone, trypton, and a decomposition product of casein.

Preferably, the cultivation is carried out under aerobic conditions. Usually, by performing the cultivation at a temperature of 15° to 45° C., preferably 20° to 35° C., for 2 to 10 days while adjusting the pH of the culture medium to 3–8, preferably 3.5–7, SAM is formed and accumulated in the microbial cells.

According to the process of this invention, the microbial cells are separated from the culture medium after the cultivation, and thereafter SAM is extracted from the microbial cells and purified. Methods known per se can be used in these steps. For example, centrifugal separation or filtration may be applied to the separation of the microbial cells from the culture medium. In obtaining SAM from the microbial cells, it is possible to extract SAM from the cells by using an extracting agent such as perchloric acid, hydrochloric acid, sulfuric acid, formic acid, acetic acid, formate esters, acetate esters, or ethanol, and purify SAM in the extract in a customary manner. There is no particular restriction on the method of purifying SAM. For example, there can be used, either alone or in combination, a chromatographic method using activated carbon, strongly acidic cation exchange resins, weakly acidic cation exchange resins or chelate resins; a method comprising precipitating SAM with reinecke salt, picric acid, phosphotungstic acid, picrolonic acid, etc., and a method comprising precipitating SAM using an organic solvent such as acetone or ethanol. In order to obtain SAM in a stabilized form, it is the general practice to add an acid such as sulfuric acid, p-toluenesulfonic acid or sulfosalicyclic acid and recover SAM as a salt or double salt.

The microbial cells of this invention are convenient for transportation of unstable SAM since they contain SAM in high concentrations. Furthermore, since these microbial cells contain only low concentrations of impurities troublesome to separate from SAM, it is easy to purify SAM, and consequently, SAM of high purity can be recovered with good efficiency.

The following examples illustrate the present invention more specifically.

EXAMPLE 1

One loopful of each of the microorganism strains indicated in Table 1 which had been grown for 2 days in an agar slant culture medium (pH 6.0) composed of 5 g/dl of glucose, 0.5 g/dl of polypeptone, 0.4 g/dl of $KH_2PO_4$, 0.4 g/dl of $K_2HPO_4$, 0.02 g/dl of $MgSO_4.7H_2O$, 0.2 g/dl of yeast extract and 2 g/dl of agar was inoculated in 10 ml of a heat sterilized culture medium adjusted to pH 6.0 and composed of 10 g/dl of sucrose, 1 g/dl of yeast extract, 0.4 g/dl of $KH_2PO_4$, 0.01 g/dl of $MgSO_4.7H_2O$, 1.0 g/dl of L-methionine, 0.25 mg/dl of $ZnSO_4.7H_2O$ and 1.25 mg/dl of $MnSO_4.4-6H_2O$, and cultivated with shaking at 28° C. for 4 days.

The microbial cells were collected by centrifugal separation, washed with physiological saline, suspended in 1.5N perchloric acid, and shaken at room temperature for 1 hour to extract SAM. The extract was subjected to paper chromatography and high-performance liquid chromatography to determine SAM, adenine (Ad for short), S-adenosyl homocysteine (SAH for short) and methylthioadenosine (MTA for short). The results are shown in Table 1.

TABLE 1

| Run No. | Microorganism strain | | Amount of SAM based on the dry cells (wt. %) | Amount of Ad* | Amount of SAH* | Amount of MTA* |
|---|---|---|---|---|---|---|
| Invention | | | | | | |
| 1-1 | (Saccharomyces | IFO 2342 | 14.8 | $2.5 \times 10^{-3}$ | 0.06 | 0.03 |
| 1-2 | cerevisiae) | IFO 2343 | 12.9 | $3.8 \times 10^{-3}$ | 0.13 | 0.08 |
| 1-3 | | IFO 2345 | 13.0 | $6.2 \times 10^{-3}$ | 0.09 | 0.04 |
| 1-4 | | IFO 2346 | 19.1 | $1.9 \times 10^{-3}$ | 0.06 | 0.02 |
| 1-5 | | IFO 2347 | 16.7 | $8.3 \times 10^{-3}$ | 0.06 | 0.03 |
| 1-6 | Yeast of Sake Kyokai No. 9 | | 18.5 | $2.7 \times 10^{-3}$ | 0.06 | 0.07 |
| Control | | | | | | |
| 1-7 | (Saccharomyces | IFO 0259 | 3.1 | $9.6 \times 10^{-2}$ | 1.6 | 0.54 |
| 1-8 | cerevisiae) | IFO 1346 | 4.0 | $5.3 \times 10^{-2}$ | 1.4 | 0.33 |
| 1-9 | | IAM 4175 | 1.8 | $8.8 \times 10^{-2}$ | 3.5 | 0.69 |
| 1-10 | | IAM 4274 | 5.3 | $5.9 \times 10^{-2}$ | 1.4 | 0.90 |
| 1-11 | | IFO 2003 | 5.1 | $4.9 \times 10^{-2}$ | 1.7 | 0.34 |
| 1-12 | | IFO 2363 | 2.1 | $7.3 \times 10^{-2}$ | 3.1 | 0.47 |

*The relative values calculated when the amount of SAM is taken as 100.

The results given in Table 1 show that when the content of SAM based on the dry cells is more than 12%, the contents of impurities difficult to separate from SAM are small.

EXAMPLE 2

Microbial cells having different contents of SAM based on the weight of the dry cells were prepared by cultivating Saccharomyces cerevisiae IFO 2346 in the same culture medium as in Example 1 except that the cultivation time, the pH of the culture medium and the cultivation temperature were changed. The resulting microbial cells were extracted and analyzed by the same methods as described in Example 1. The results are shown in Table 2.

TABLE 2

| Run No. | Content SAM based on the dry cells (wt. %) | Amount of Ad (*) | Amount of SAH (*) | Amount of MTA (*) |
|---|---|---|---|---|
| Invention | | | | |
| 2-1 | 19.9 | $1.8 \times 10^{-3}$ | 0.06 | 0.01 |
| 2-2 | 19.1 | $1.9 \times 10^{-3}$ | 0.06 | 0.02 |
| 2-3 | 16.3 | $3.1 \times 10^{-3}$ | 0.08 | 0.04 |
| 2-4 | 15.1 | $6.2 \times 10^{-3}$ | 0.28 | 0.04 |
| 2-5 | 12.0 | $9.3 \times 10^{-3}$ | 0.30 | 0.07 |
| Control | | | | |
| 2-6 | 6.2 | $4.9 \times 10^{-2}$ | 9.9 | 0.33 |
| 2-7 | 3.5 | $5.4 \times 10^{-2}$ | 1.4 | 0.33 |
| 2-8 | 1.8 | $9.6 \times 10^{-2}$ | 1.7 | 0.37 |

(*)The relative values calculated when the amount of SAM is taken as 100.

EXAMPLE 3

One loopful of each of the microorganism strains indicated in Table 3 was inoculated in 10 ml of a heat-sterilized culture medium adjusted to pH 6.0 and composed of 5 g/dl of glucose, 0.5 g/dl of polypeptone, 0.4 g/dl of $KH_2PO_4$, 0.4 g/dl of $K_2HPO_4$, 0.02 g/dl of $MgSO_4.7H_2O$ and 0.2 g/dl of yeast extract, and cultivated with shaking at 28° C. for 24 hours.

One liter of a culture medium adjusted to pH 6.0 and composed of 10 g/dl of sucrose, 1 g/dl of yeast extract, 0.4 g/dl of $KH_2PO_4$, 0.01 g/dl of $MgSO_4.7H_2O$, 1.5 g/dl of urea (separately sterilized), 0.75 g/dl of L-methionine, 0.02 g/dl of $CaCl_2.2H_2O$, 0.25 mg/dl of $ZnSO_4.7H_2O$, 0.25 mg/dl of $FeSO_4.7H_2O$, 125 mg/dl of $MnSO_4.4$–$6H_2O$, 2 μg/dl of $CuSO_4.5H_2O$, 2 μg/dl of $H_3BO_3$, 0.2 μg/dl of $CoCl_2.6H_2O$ and 1 μg/dl of KI was put in a 2-liter fermentor and sterilized. Then, 5 ml of the seed culture broth prepared as above was inoculated in the culture medium and cultivated at 28° C. for 72 hours with aeration and agitation.

After the cultivation, the microbial cells were collected by centrifugal separation, washed once with physiological saline, suspended in 100 ml of 1.5N perchloric acid, and shaken at room temperature for 1 hour. The suspension was then centrifuged to remove the microbial cells, and the resulting liquid was adjusted to pH 4.5 by adding potassium hydrogen carbonate. The resulting precipitate of potassium perchlorate was removed by centrifugal separation to give an extract containing SAM. The amount of SAM in the extract was determined, and the amount of SAM based on the dry cells is shown in Table 3.

The extract in an amount of 0.2 g as SAM was passed through a column filled with 50 ml of Amberlite IRC-50 ($H^+$ form), a weakly acidic cation exchange resin, to cause adsorption of SAM. 0.005N acetic acid was passed through the column to wash it until the absorbance at 260 nm of the eluate became less than 0.1. Thus, impurities were removed. The amount of 0.005N acetic acid required at this time is shown in Table 3. Then, 0.1N sulfuric acid was passed through the column, and SAM was eluted until the absorbance at 260 nm of the eluate became less than 0.05. The eluate was treated with Amberlite IRA 900 resin ($OH^-$ form) to adjust its pH to 3.0, and then lyophilized to obtain SAM sulfate. The ratio of recovery of SAM is shown in Table 3. The purity of SAM was measured by cellulose thin-layer chromatography, paper chromatography and high-performance liquid chromatography, and is shown in Table 3.

TABLE 3

| Run No. | Microorganism strain | | Amount of SAM based on the dry cells (wt. %) | Amount of 0.005 N acetic acid required to remove the impurities (ml) | Recovery ratio of SAM (%) | Purity of SAM (%)[*1] | Ninhydrin reaction of substances other than SAM[*2] |
|---|---|---|---|---|---|---|---|
| Invention | | | | | | | |
| 3-1 | (Saccharomyces | IFO 2343 | 12.1 | 980 | 94 | 95 | trace (±) |
| 3-2 | cerevisiae) | IFO 2346 | 18.8 | 770 | 96 | 96 | " |
| 3-3 | | IFO 2347 | 16.7 | 890 | 94 | 95 | " |
| Control | | | | | | | |
| 3-4 | (Saccharomyces | IFO 1346 | 3.1 | 1910 | 86 | 84 | ++ |
| 3-5 | cerevisiae) | IAM 4274 | 4.0 | 1760 | 86 | 83 | ++ |
| 3-6 | | IFO 2363 | 2.1 | 2440 | 81 | 86 | ++ |

[*1]Purity of SAM
After development by two-dimensional paper chromatography, a spot attributed to SAM was detected. Then, a portion corresponding to the spot of SAM was cut off, and SAM was extracted with 0.1 N hydrochloric acid from the cut portion. The purity of SAM was calculated from the molecular extinction coefficient (15400) of SAM at 260 nm.

[*2]Ninhydrin reaction of substances other than SAM
After development by two-dimensional cellulose thin-layer chromatography, the presence of spots attributed to substances other than SAM detected by color reaction of ninhydrin was determined.

It is seen from Table 3 that in the present invention, the amount of the eluate required to remove impurities can be small, and the ratio of recovery of SAM and the purity of SAM are very good.

What is claimed is:

1. A substantially biologically pure culture of yeast of the genus Saccharomyces which contains at least 10% S-adenosyl methionine by weight, based on the dry cell weight of the culture, and being substantially free of methylthioadenosine.

2. The culture of claim 1 wherein the yeast of genus Saccharomyces is a yeast belonging to Sacchuromyces cerevisiae.

3. The culture of claim 2 wherein the yeast belonging to Saccharomyces cerevisiae is selected from the group consisting of Saccharomyces cerevisiae IFO 2342, Saccharomyces cerevisiae IFO 2343, Saccharomyces cerevisiae IFO 2345, Saccharomyces cerevisiae IFO 2346, Saccharomyces cerevisiae IFO 2347, and Yeast of Sake Kyokai No. 4.

4. The culture of claim 3 containing at least 12% by weight, based on the weight of the dry cell, of S-adenosyl methionine.

5. The culture of claim 4 wherein the content of methylthioadenosine is at most 0.08 part by weight per 100 parts by weight of S-adenosyl methionine.

6. The culture of claim 1 containing at least 12% by weight, based on the dry cell, of S-adenosyl methionine.

7. The culture of claim 6 wherein the content of methylthioadenosine is at most 0.08 part by weight per 100 parts by weight of S-adenosyl methionine.

8. The cell of claim 1 wherein the content of methylthioadenosine is at most 0.08 part by weight per 100 parts by weight of S-adenosyl methionine.

9. A process for producing S-adenosyl methionine, which comprises cultivating a yeast microorganism belonging to the genus Saccharomyces having the ability to produce S-adenosyl methionine at a temperature of 15° to 45° C. under aerobic conditions in a liquid culture medium at a pH of from 3 to 8 and containing an effective amount of methionine to obtain the cells containing at least 10% S-adenosyl methionine by weight based on the dry yeast cells, and being substantially free of methylthioadenosine, separating the yeast cells from the culture medium and thereafter obtaining S-adenosyl methionine in a stable form from the yeast cells.

10. The process of claim 9 wherein yeast culture belongs to *Saccharomyces cerevisiae*.

11. The process of claim 9 wherein the yeast belonging to the genus *Saccharomyces cerevisiae* is selected from the group consisting of *Saccharomyces cerevisiae* IFO 2342, *Saccharomyces cerevisiae* IFO 2343, *Saccharomyces cerevisiae* IFO 2345, *Saccharomyces cerevisiae* IFO 2346, *Saccharomyces cerevisiae* IFO 2347, and Yeast of Sake Kyokai No. 9.

12. The process of claim 11 wherein the yeast cells are cultivated to contain at least 12% by weight, based on the dry yeast cell, of S-adenosyl methionine.

13. The process of claim 12 wherein the yeast cells containing at least 12% by weight of S-adenosyl methionine contain no more than 0.08 part by weight of methylthioadenosine per 100 parts by weight of S-adenosyl methionine.

14. The process of claim 9 wherein the yeast cells are cultivated to contain at least 12% by weight, based on the dry yeast cells, of S-adenosyl methionine.

15. The process of claim 14 wherein the cells containing at least 12% by weight of S-adenosyl methionine contain no more than 0.08 part by weight of methylthioadenosine per 100 parts by weight of S-adenosyl methionine.

16. The process of claim 9 wherein the yeast cells containing at least 10% by weight of S-adenosyl methionine contain no more than 0.08 part by weight of methylthioadenosine per 100 parts by weight of S-adenosyl methionine.

* * * * *

UNITED STATES PATENT AND TRADEMARK OFFICE
CERTIFICATE OF CORRECTION

PATENT NO. : 4,562,149

DATED : December 31, 1985

INVENTOR(S) : SHOZO SHIOZAKI, ET AL.

It is certified that error appears in the above-identified patent and that said Letters Patent is hereby corrected as shown below:

IN THE CLAIMS

Claim 2, line 2, (column 6, line 34),
   delete "Sacchuromyces", insert --Saccharomyces--.

Claim 3, line 7, (column 6, line 42),
   delete "No. 4", insert --No. 9--.

Signed and Sealed this

Fourth Day of March 1986

[SEAL]

Attest:

DONALD J. QUIGG

Attesting Officer

Commissioner of Patents and Trademarks